United States Patent
Such et al.

(10) Patent No.: US 8,083,674 B2
(45) Date of Patent: Dec. 27, 2011

(54) POWER SAVING UPLINK FOR BIOSENSORS

(75) Inventors: Olaf Such, Aachen (DE); Gereon Vogtmeier, Aachen (DE); Josef Lauter, Geilenkirchen (DE); Harald Reiter, Aachen (DE); Christian Reichinger, Neutraubling (DE); Ralf Schmidt, Aachen (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 253 days.

(21) Appl. No.: 10/530,494

(22) PCT Filed: Sep. 18, 2003

(86) PCT No.: PCT/IB03/04152
§ 371 (c)(1),
(2), (4) Date: Apr. 6, 2005

(87) PCT Pub. No.: WO2004/032736
PCT Pub. Date: Apr. 22, 2004

(65) Prior Publication Data
US 2005/0261556 A1    Nov. 24, 2005

(30) Foreign Application Priority Data
Oct. 11, 2002  (EP) .................................. 02079214

(51) Int. Cl.
*A61B 5/00*    (2006.01)

(52) U.S. Cl. ............................ 600/300; 340/3.1; 128/920
(58) Field of Classification Search .................. 600/300; 128/903–905, 920; 340/539.12, 3.1
See application file for complete search history.

(56) References Cited

U.S. PATENT DOCUMENTS

| 4,987,897 | A  | * | 1/1991  | Funke .............................. 607/32 |
| 6,289,238 | B1 | * | 9/2001  | Besson et al. .................. 600/509 |
| 6,315,719 | B1 | * | 11/2001 | Rode et al. ..................... 600/300 |
| 7,138,902 | B2 | * | 11/2006 | Menard ........................ 340/5.53 |

FOREIGN PATENT DOCUMENTS

| WO | WO0178831 A2 | 10/2001 |
| WO | WO0178831 A3 | 10/2001 |

* cited by examiner

*Primary Examiner* — Sam Yao
*Assistant Examiner* — Kai Rajan

(57) ABSTRACT

A system for monitoring a physiological condition of an individual. The system (1) comprises sensing means (3) arranged to pick up a first signal (M) in a first mode of the system, said first signal being representative of the physiological condition and to forward the first signal to a signal processing unit (33). The system comprises an actuatable control unit (2) positioned remote from the signal processing unit, the control unit (2) being suitable to generate a second signal (T) arranged to be superimposed on the first signal (M). The signal processing unit (33, 37) is arranged to decode the second signal and to make the system enter into a second mode upon receipt of the second signal (T).

20 Claims, 3 Drawing Sheets

Figure 1:
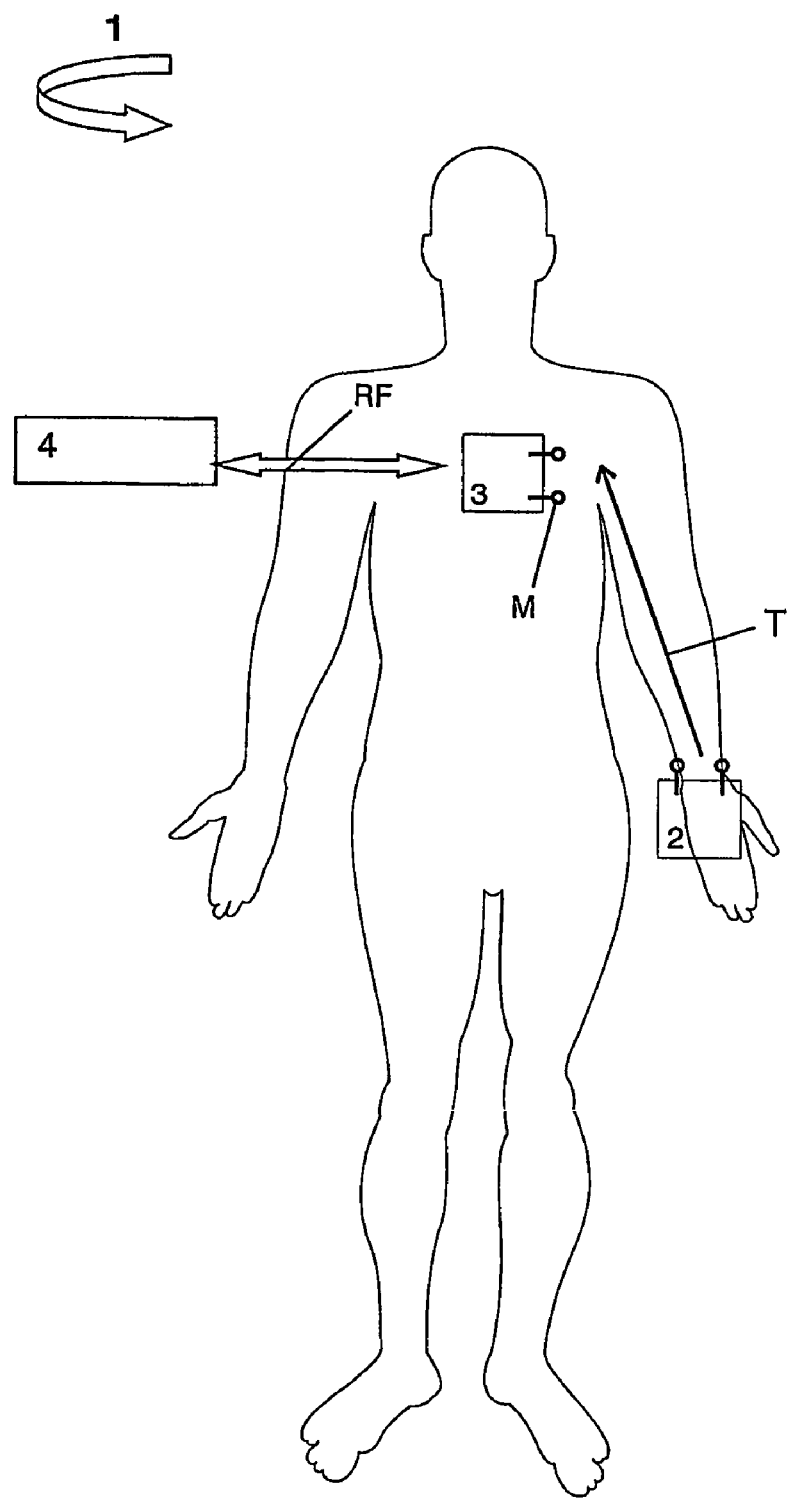

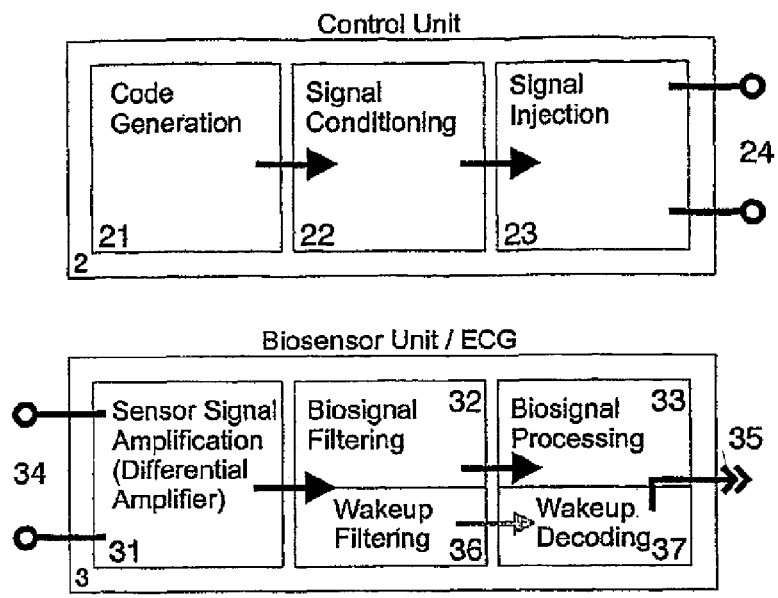
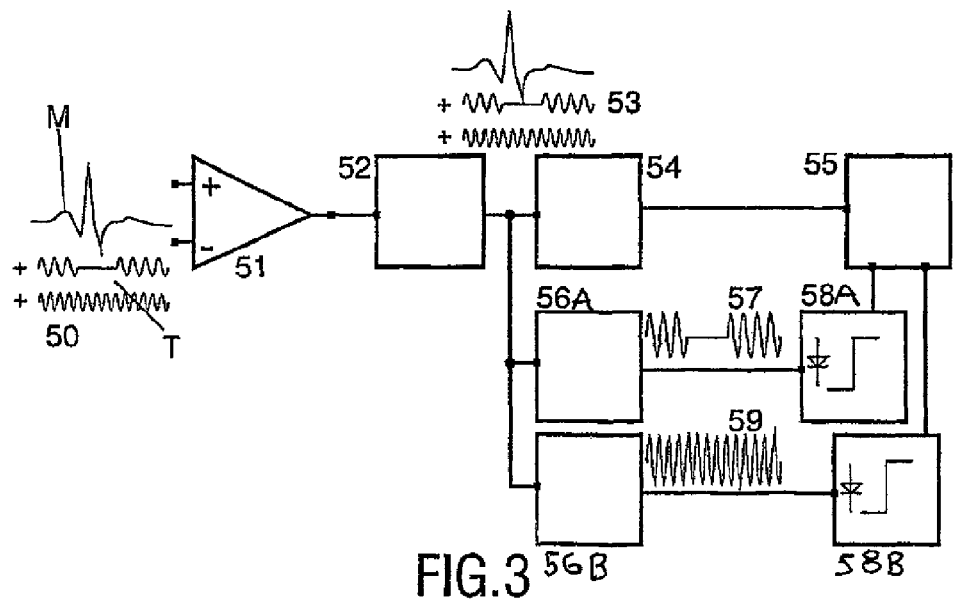
FIG.2
FIG.3

POWER SAVING UPLINK FOR BIOSENSORS

The invention relates to a system for monitoring a physiological condition of an individual, comprising sensing means arranged to pick up a first signal in a first mode of the system, said first signal being representative of said physiological condition and to forward said first signal to a signal processing unit.

The invention further relates to a control unit conceived to be suitable for a personal monitoring system, said personal monitoring system being arranged to pick-up a signal representative of a physiological condition of an individual.

A system as set forth in the opening paragraph is known from WO 01/78831. The known system is arranged to monitor a physiological condition of an individual by means of a set of sensors, further referred to as sensing means, positioned in a physical contact with the individual. The sensing means is arranged to pick up a signal representative of the individual's physiological condition. Such a signal can be a heart rate, a respiration rate or other suitable signal measurable on the individual's body. The known system further comprises a processing unit arranged to analyze the signal from the set of electrodes. In order to perform maintenance procedures the known system comprises an RF-interface to a base unit, said base unit being arranged to emit a trigger signal which upon receipt by the monitoring system sets it into a service mode. The operations performed by the monitoring system in the service mode comprise registration information, transmission frequency commands, electronics set-up, transmitter control commands, power saving mode and other suitable configuring commands. The known monitoring system is portable and is powered by a battery.

A disadvantage of the known system is a high power consumption due to a constantly functioning RF-receive channel waiting for the trigger signal from the base unit. This leads to a necessity of a frequent battery replacement or recharging, leading to increased system cost and reduced reliability.

It is an object of the invention to provide a monitoring system with reduced power consumption. The system according to the invention is characterized in that said system comprises an actuatable control unit positioned remote from said signal processing unit, said control unit being suitable to generate a second signal arranged to be superimposed on the first signal, said signal processing unit being arranged to decode the second signal and to enter into a second mode upon a receipt of the second signal. The invention is based on an insight that most-monitoring systems comprise a data receiving channel operating in a continuous mode to receive individual's data, defined as the first signal. For example, in case a cardiac activity of the individual is being monitored, the sensing means comprises a receiving channel for the ECG-data, said channel comprising a sensitive differential amplifier operating at some tens of Hz and microvolts of normal signal. Since this channel is always active it is advantageous to use this channel as an amplifier for a receipt of a trigger signal to switch the monitoring system into a different mode. For the sake of clearness the data collection mode is referred to as the first mode and any other mode is referred to as the second mode. An example of the second mode is the service mode where the system performs self-maintenance operations, like prepare uploading of parameters or program code to the monitoring system, initiation of a response to check operating conditions, initiation of a self test of the monitoring system, battery check, shutdown and power off operations etc. Thus, it is advantageous to arrange the control unit to initiate a switching by the monitoring system into a second mode. Therefore, the control unit must have provisions to generate a code that can be added or superimposed to the first signal. Preferably the code, or the second signal is arranged as a disturbance on the first signal. This disturbance can be decoded by the processing unit of the monitoring system followed by the monitoring system entering the second mode of operation. It is possible that upon the system entering the second mode a dedicated wakeup sequence is started which may initiate further communication. It must be noted that this action may consume much more power than normal operation, but since it is only applied with relatively low duty cycles, for example of less than 0.1%, this will not be a limiting factor of the battery life, thus improving the system reliability.

An embodiment of the system according to the invention is characterized in that the control unit comprises an electrode to be arranged in a contact with the individual's skin, said electrode being arranged to transmit the second signal. This technical measure is based on an insight that the human body is a conductive medium suitable to conduct electric signals induced from outside. Therefore, by transmitting a second signal and by conducting it through the individual's skin by means of the electrode a superposition of the second signal upon the first signal is achieved. To perform this operation common electrodes will suffice, the thus injected second signal will propagate substantially on the surface of the individual.

A further embodiment of the system according to the invention is characterized in that that the system further comprises an RF-link arranged to establish a wireless communication to a remote base unit, the second signal being a trigger signal for the RF-link to perform a predetermined operation. According to this technical measure the monitoring system performs an RP-transmission and an RF-receipt only upon a receipt of the second signal. Therefore, the power consumption of the monitoring system is reduced. A design of the RF-link lies within the technical skills of a person skilled in the art and will not be described here in detail. An example of the predetermined operation for the RF-link is an initiation of a suitable data receipt and/or data transmission protocol, the remote base unit being arranged to respond upon a corresponding communication protocol initiated by the RF-link.

A still further embodiment of the system according to the invention is characterized in that the second signal comprises data to be processed by the signal processing unit. It is advantageous to arrange the second signal that it comprises actual data to be processed by the signal processing means. An example of such actual data is system set-up formation, like patient identification, date or the like. According to this technical measure there is no need for the RF-link to be actuated, the data is entered into the monitoring system by the user bypassing a communication with the base unit. This technical measure further improves the power consumption by the system.

A still further embodiment of the system according to the invention is characterized in that the second signal has substantially the same bandwidth as the first signal, the amplitude of the second signal being at least one order of magnitude smaller than the amplitude of the first signal. It is advantageous to arrange the second signal so that it's bandwidth coincides with the bandwidth of the first signal. In this case the electronics circuitry of the monitoring system can be kept simple.

A control unit according to the invention is characterized in that said control unit is arranged to control the personal monitoring system by means of a generation of a suitable trigger signal, and by superimposing said trigger signal on the signal representative of the monitored physiological condition. The control unit according to the invention can be worn by the user, for example on an extremity or can be integrated into clothing. The user interface of such a control unit can be advantageously arranged for user to be able to select the service mode, or to enter data into the monitoring system manually via a suitably arranged control panel.

An embodiment of the control unit according to the invention is characterized in that the control unit comprises an electrode to be arranged in contact with the individual's skin, said electrode being arranged to transmit the trigger signal. By means of the electrode place in physical contact with the individual's skin a superposition of the second signal and the first signal can be realized.

An embodiment of the control unit according to the invention is characterized in that the control unit comprises a user interface arranged to operate said control unit in a manual mode. Preferably the user interface comprises an actuatable data input port and a display. An example of the actuatable data port is a keyboard, which can be actuated by the user. This is particularly advantageous in case the user wants to edit the administrative data stored in the memory of the control unit. Also, the user can alter the date and time, while passing through time zones.

These and other aspects of the invention will be discussed in more detail with reference to figures.

FIG. 1 present a schematic view of an embodiment of the system for monitoring a physiological condition of an individual according to the invention.

FIG. 2 presents a schematic view of an embodiment of a technical realization of the system according to the invention.

FIG. 3 presents schematically an embodiment of the monitoring means for in band signaling mode.

Figure 4:
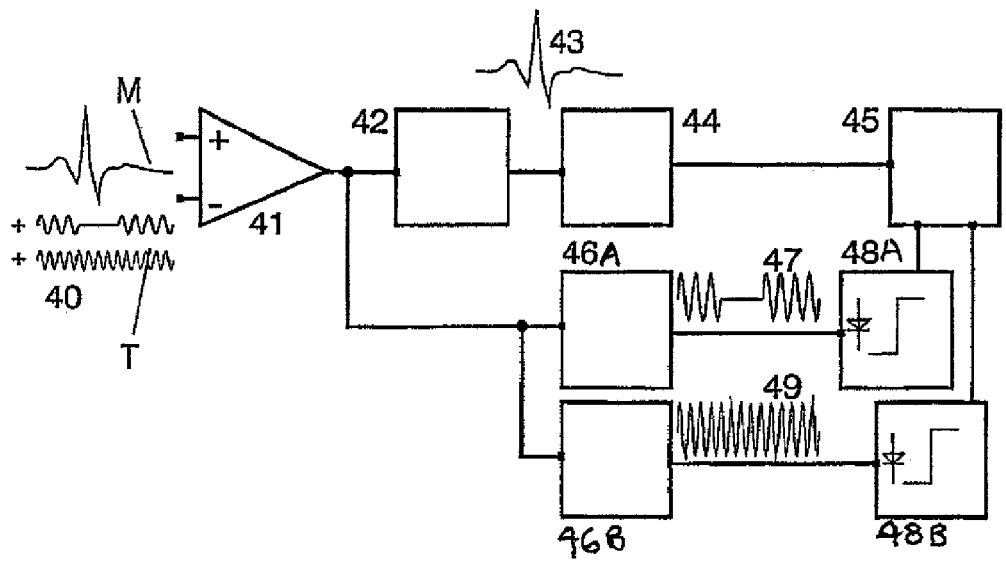

FIG. 4 presents schematically an embodiment of the monitoring means for out of band signaling mode.

Figure 5:
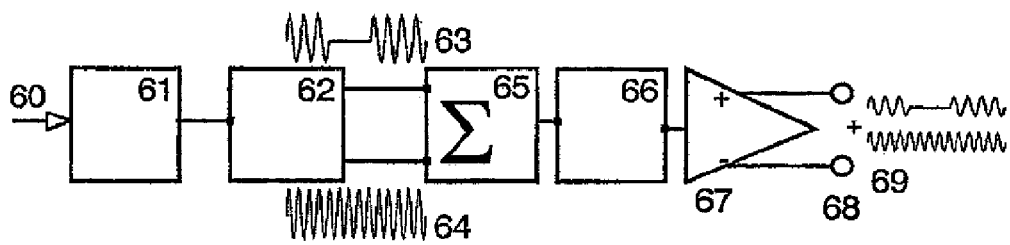

FIG. 5 presents in a schematic way an embodiment of a transmission part of the control unit according to the invention.

Figure 6:
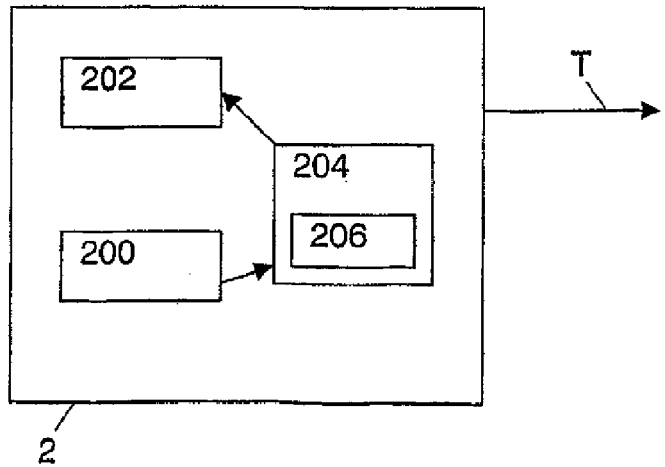

FIG. 6 shows schematically an embodiment of the user interface of the control unit according to the invention.

FIG. 1 shows in a schematic way an embodiment of the system (1) for monitoring a physiological condition of an individual according to the invention. The individual is supplied with a set of biosensors (3) adapted for monitoring the targeted physiological condition. An example of such physiological condition is a heart rate, temperature, blood flow, electroencephalogram, etc. The placement of the set of biosensors (3) is performed according to the targeted physiological condition. FIG. 1 shows an example of the placement of the set of biosensors for monitoring of a cardiac activity, in which case the biosensors are placed in the thorax area. The functioning of the set of biosensors (3) is known to the person skilled in the art and, therefore, will not be explained in detail. For purposes of a durable monitoring, the set of biosensors (3) has to be worn continuously. It is desirable that the electronic configuration set of biosensors (3) is updated with some preset maintenance intervals. The update of the electronic configuration is performed by means of an RF-communication protocol of a processor unit (not shown) of the set of biosensors (3), the processor unit being included in a base unit (4) located remotely from the set of biosensors (3). According to the invention the system (1) is supplied with a remote controle unit (2) which sends a trigger signal to the set of biosensors (3) in order to enable, for example a service mode for the biosensors (3). The trigger signal (T) is induced by the control unit in the individual by means of electrodes (not shown). The trigger signal (T) is arranged in such a way that it is superimposed on the measured signal and is decodable by the processor unit of the set of biosensors (3). Upon the decoding of the trigger signal (T) the processor unit initiates a predetermined operation. For example the system can be actuated to perform the following operations: prepare uploading of parameters or program code to the biosensors (3) from the base unit (4), initiate response to check working conditions, start self test of biosensors (3), check battery state, shut down and power off, update date and time, etc. The initiation of the RF-link, schematically represented by a two-directional arrow, is performed only after the trigger signal (T) is received by the biosensors (3) and is decoded by the processing unit of the biosensors (3). In this way the system saves power as the power consuming operation of the RF-communication is performed only upon request.

FIG. 2 presents a schematic view of an embodiment of a technical realization of the system according to the invention. The Control Unit (2) worn on the body comprises a code generator (21) which generates a trigger signal with a corresponding trigger code. This is then conditioned by a conditioning unit (22) in a way suitable for filtering in the Biosensor Unit (3). The signal then is injected into the body by means of amplifier (23) and electrode (24) in order to generate a signal at the Biosensor Unit (3) that is compatible with its signal conditioning circuitry. In the case of ECG, this will be an electrical field generating a signal at the input electrodes (34) that should be at the most in the order of magnitude of the real ECG signal and lie in substantially similar bandwidth range but will have much smaller amplitude in order to keep the dynamic range of the input differential amplifier (31) low. This is acceptable due to the filtering/decoding done, as the trigger code is preferably arranged with a known and expected form and timing, which enables it to be discriminated from a higher overlaid signal. The biosensor unit (3) comprises biosignal filtering unit (32) and processing unit (33). Next to this the Biosensor unit (3) is supplied with a trigger filtering unit (36) and a trigger decoding unit (37). In case of in band signaling the processing circuitry (32,33,36, 37) is supplied with routines to decode the trigger code sequence. If out of band signaling is realized, also an additional filter to limit the bandwidth can be employed, which costs little in terms of power or component size or price. This simplifies the decoding and safeguards the ECG signal from severe disruptions even during the (seldom) trigger phase. Also, in certain cases, this may enable very low power realizations, as the processing unit (33) may be in a "sleep" mode for most of the time (as long as there is neither a wakeup nor an event on the ECG that it must handle).

FIG. 3 presents schematically an embodiment of the monitoring means for in band signaling mode. The transmitter of the control unit (not shown) overlays the trigger signal (T) on top of the biosignal (M), here an ECG. The trigger signal is a dual tone signal preferably of 29.5 Hz continuous wave and 22.5 Hz on-off keyed data. The sum of both (50) is detected at the input of the biosensor, in the case of an ECG a differential amplifier (51). The Band Pass Filter (52) passes the amplified biosignal plus the trigger signal (53) to the Analog to Digital Converter (54), which is processed by the microcontroller (55). The Band Pass Filters (56A, 56B) select and amplify the separate frequency components of the trigger signal (T), so that at their output, for example the 29.5 Hz continuous wave (59) and 22.5 Hz on-off keyed data (57) are available. These are then each passed on to a demodulator, which could be comprise a full wave rectifier with following comparators (58A, 58B). The comparators (58A, 58B) give digital outputs to the microcontroller (55), whenever a signal component in this frequency range is detected. By decoding a data stream coded as a digital word on these signals, control functions can be realized, and the biosensor can be brought to a state as desired by the transmitting device that otherwise has no connection to the sensor. The trigger signal (T) superimposed on the biosignal (M) is either so small that it does not disturb the measurement, or else it may be removed by signal processing. Many applications also do not require a continuous reading of the biosignal, and the control signal, taking only a short duration, may be interpreted as an artifact in the biosignal measuring circuitry, thus introducing no confusion to the system.

FIG. 4 presents schematically an embodiment of the monitoring means for out of band signaling mode. The transmitter of the control unit (not shown) overlays the trigger signal (T) on top of the biosignal (M), here an ECG. The trigger signal is a dual tone signal, preferably of 129.5 Hz continuous wave and 122.5 Hz on-off keyed data. The sum of both signals (40) is detected at the input of the biosensor, in the case of an ECG a differential amplifier (41). A sand Pass Filter (42) removes the control signal and passes the amplified biosignal (43) to an Analog to Digital Converter (44), which is processed by a microcontroller (45). Further Band Pass Filters (46A, 46B) select and amplify the separate frequency components of the control signal, so that at their output, for example the 129.5 Hz continuous wave (49) and 122.5 Hz on-off keyed data (47) are available. These are then each passed on to a demodulator, which could be a full wave rectifier with a following comparators (48A, 48B). These then give digital outputs to the microcontroller (45), whenever a signal component in this frequency range is detected. The control functions can be realized by decoding a data stream coded as a digital word on these signals. Thus, the biosensor can be brought to a state as desired by the transmitting device that otherwise has no connection to the sensor.

FIG. 5 presents in a schematic way an embodiment of a transmission part of the control unit according to the invention. The control signal (60) causes a microcontroller (61) to start the control word transmission. In the present embodiment, this is done by writing the appropriate coded signals to a Digital-to-Analog Converter (62), which can be for example a multi-channel converter. The dual tone signal of, for example 29.5 Hz continuous wave and 22.5 Hz on-off keyed data (64,63) is then summed with a summing amplifier (65) and filtered by a low pass filter (66) to filter out overtones and aliasing noise. The signal is then made symmetrical by a single-end to differential driver (67), which drives the electrodes (68), which in turn conduct the trigger signal (69) into the body of the individual being monitored. This will be in the order of Volts, very low current in the order of microAmperes, and have no adverse effect on body function or implantable devices. Electrodes will preferably be of the dry type, or simple metallic contacts on a wristband of a wristwatch-like carrier of the control unit.

FIG. 6 shows schematically an embodiment of the user interface of the control unit according to the invention. For the convenience of the user the control unit (2) is arranged with a keyboard (200) and a display (202) to show the information being altered manually. The control unit (2) comprises a processor (204) arranged to initiate a transmission of the trigger signal (T) upon request of the user or in a predetermined time interval. The processor (204) is preferably arranged to warn the user via the display (202) upon the transmission of the trigger signal, thus ensuring that the user is informed that the biosensors (not shown) are actuated to work in a different mode. The processor (204) is preferably arranged to store a set of coded trigger signals in a look-up table (206), which can be addressed upon request. The trigger signal (T) can be arranged to transmit actual data, edited by the user, for example day, time and administrative data, or it can comprise a coded command to the processing unit of the biosensors (not shown) to actuate the RF-communication protocol with a base unit (not shown) in order to download service information.

The invention claimed is:

1. A system for monitoring a physiological condition of an individual, comprising:
a sensor including a signal processing unit and an input arranged to pick up a first signal in a first mode of the system, the first signal being representative of the physiological condition and to forward the first signal to the signal processing unit, a control unit arranged to be positioned remote from the signal processing unit and to be selectively actuated to effect a system mode change, the control unit being arranged to generate a second signal and transmit the second signal to the input of the sensor superimposed on the first signal, the signal processing unit being arranged to decode the second signal and to make the system enter into a second mode upon receipt of the second signal, wherein the input of the sensor is arranged to receive the second signal as a disturbance of the first signal.

2. The system according to claim 1, wherein the control unit comprises an electrode arranged to be in contact with the individual's skin, the electrode being arranged to transmit the second signal.

3. The system according to claim 2, wherein the system further comprises an RF-link arranged to establish a wireless communication to a remote base unit, the second signal being a trigger signal for the RF-link to perform a predetermined operation.

4. The system according to claim 2, wherein the second signal comprises data to be processed by the signal processing unit.

5. The system according to claim 1, wherein the second signal has a same bandwidth as the first signal, the amplitude of the second signal being at least one order of magnitude smaller than the amplitude of the first signal.

6. The personal monitoring system according to claim 1, wherein upon receipt of the trigger signal, the signal processing unit is arranged to perform a dedicated wakeup sequence.

7. The personal monitoring system according to claim 6, wherein the dedicated wake-up sequence includes turning on of an RF-link that is otherwise always in an off-state unless responding to a prior dedicated wake-up sequence.

8. The personal monitoring system according to claim 1, wherein the control unit is arranged to transmit the second signal as a dual-tone signal.

9. The personal monitoring system according to claim 8, wherein the dual-tone signal is substantially a 29.5 Hz continuous wave and 22.5 Hz on-off keyed signal.

10. The personal monitoring system according to claim 8, wherein the dual-tone signal is substantially a 129.5 Hz continuous wave and 122.5 Hz on-off keyed signal.

11. A personal monitoring system for selectively actuating a personal monitoring system, the personal monitoring system including an input being arranged to pick up a signal representative of a physiological condition of an individual, the personal monitoring system comprising a control unit arranged to control the personal monitoring system by a generation of a suitable trigger signal which is transmitted to the input of the personal monitoring system, and arranged to superimpose the trigger signal on the signal representative of the monitored physiological condition to control an operating mode of the monitoring system, wherein the control unit is arranged to produce the trigger signal as a disturbance of the signal representative of the monitored physiological condition.

12. The personal monitoring system according to claim 11, wherein the control unit comprises an electrode arranged to be in contact with the individual's skin, the electrode being arranged to transmit the trigger signal.

13. The personal monitoring system according to claim 11, wherein the control unit comprises a user interface arranged to operate the control unit in a manual mode.

14. The personal monitoring system according to claim 13, wherein the control unit comprises a data input port and a display.

15. The personal monitoring system according to claim 11, wherein upon receipt of the trigger signal, the personal monitoring system is arranged to perform a dedicated wakeup sequence.

16. The personal monitoring system according to claim 15, wherein the dedicated wake-up sequence includes turning on of an RF-link that is otherwise always in an off-state unless responding to a prior dedicated wake-up sequence.

17. The personal monitoring system according to claim 11, wherein the control unit is arranged to transmit the trigger signal as dual-tone signal.

18. The personal monitoring system according to claim 17, wherein the dual-tone signal is substantially a 29.5 Hz continuous wave and 22.5 Hz on-off keyed signal.

19. The personal monitoring system according to claim 17, wherein the dual-tone signal is substantially a 129.5 Hz continuous wave and 122.5 Hz on-off keyed signal.

20. A system for monitoring a physiological condition of an individual, comprising:
   a sensor including a signal processing unit and an input arranged to pick up a first signal in a first mode of the system, the first signal being representative of the physiological condition of the individual, wherein the input of the sensor is arranged to forward the first signal to the signal processing unit; and
   a control unit arranged to be positioned remote from the signal processing unit and to be selectively actuated to effect a system mode change, the control unit being arranged to generate and transmit a second signal to input of the sensor superimposed on the first signal, the signal processing unit being arranged to decode the second signal and to initiate the system entering into a second mode based upon receipt of the second signal by the sensor, wherein the input of the sensor is arranged to receive the second signal as a disturbance of the first signal.

* * * * *